(12) United States Patent
Borrero et al.

(10) Patent No.: US 10,905,603 B2
(45) Date of Patent: Feb. 2, 2021

(54) SEAMLESS DISPOSABLE ABSORBENT GARMENT

(71) Applicant: Drylock Technologies NV, Zele (BE)

(72) Inventors: Ricardo Borrero, Altoona, WI (US); Michael Wayne Harris, Eau Claire, WI (US); Michael Sandor, Eau Claire, WI (US)

(73) Assignee: Drylock Technologies NV, Zele (BE)

( * ) Notice: Subject to any disclaimer, the term of this patent is extended or adjusted under 35 U.S.C. 154(b) by 1168 days.

(21) Appl. No.: 15/026,100

(22) PCT Filed: Sep. 30, 2014

(86) PCT No.: PCT/US2014/058312
§ 371 (c)(1),
(2) Date: Mar. 30, 2016

(87) PCT Pub. No.: WO2015/048745
PCT Pub. Date: Apr. 2, 2015

(65) Prior Publication Data
US 2016/0213529 A1 Jul. 28, 2016

Related U.S. Application Data

(60) Provisional application No. 61/884,697, filed on Sep. 30, 2013.

(51) Int. Cl.
*A61F 13/496* (2006.01)
*A61B 9/00* (2006.01)
*A41B 9/00* (2006.01)

(52) U.S. Cl.
CPC .......... *A61F 13/4963* (2013.01); *A41B 9/001* (2013.01); *A41B 2400/52* (2013.01); *A41B 2500/10* (2013.01)

(58) Field of Classification Search
CPC .......... A61F 13/15577; A61F 13/15707; A61F 13/15739; A61F 2013/15715;
(Continued)

(56) References Cited

U.S. PATENT DOCUMENTS 4,624,115 A * 11/1986 Safrit ..................... A41B 9/001
66/172 R
4,682,479 A 7/1987 Pernick
(Continued)

FOREIGN PATENT DOCUMENTS

| WO | WO-2015048745 A2 | 4/2015 |
| WO | WO-2015048745 A3 | 4/2015 |
| WO | WO-2015048745 A8 | 4/2015 |

OTHER PUBLICATIONS

"International Application Serial No. PCT/US2014/058312, International Preliminary Report on Patentability dated Feb. 25, 2016", 8 pgs.

(Continued)

*Primary Examiner* — Catharine L Anderson
(74) *Attorney, Agent, or Firm* — Schwegman Lundberg & Woessner, P.A.

(57) ABSTRACT

A substantially cylindrical, or tubular, garment structure can be provided using a three-dimensional or circular knitting machine, using a mold, or using an additive manufacturing process. A unit segment of the garment structure can include two waistband regions at opposite end faces of the cylindrical garment structure, and each of the waistband regions can correspond to a different one of two nested articles. Each of the two nested articles can be converted into a separate and distinct brief-style absorbent underwear assembly. In an example, a waistband region and body panel region of an absorbent underwear product can be formed using the same knitted material in a continuous, three-dimensional knitting process.

13 Claims, 8 Drawing Sheets

(58) Field of Classification Search
CPC . A41B 9/001; A41B 2400/52; A41B 2500/10;
D04B 1/18; D04B 1/243
See application file for complete search history.

(56) References Cited

U.S. PATENT DOCUMENTS

| | | | |
|---|---|---|---|
| 5,572,888 A * | 11/1996 | Browder, Jr. | D04B 1/18 |
| | | | 2/401 |
| 5,855,123 A * | 1/1999 | Albright | A41B 9/04 |
| | | | 66/177 |
| 6,041,446 A * | 3/2000 | Braunstein | A41B 9/004 |
| | | | 2/400 |
| 6,192,717 B1 | 2/2001 | Rabinowicz | |
| 6,287,169 B1 | 9/2001 | Willms | |
| 2006/0048283 A1 | 3/2006 | Sorensen | |
| 2012/0042493 A1 | 2/2012 | Schmitz | |
| 2012/0084903 A1 | 4/2012 | Roberts et al. | |

OTHER PUBLICATIONS

"International Application Serial No. PCT/US2014/058312, International Search Report dated Mar. 20, 2015", 4 pgs.
"International Application Serial No. PCT/US2014/058312, Invitation to Pay Additional Fees and Partial Search Report dated Jan. 14, 2015", 2 pgs.
"International Application Serial No. PCT/US2014/058312, Written Opinion dated Mar. 20, 2015", 23 pgs.

* cited by examiner

SEAMLESS DISPOSABLE ABSORBENT GARMENT

CROSS-REFERENCE TO RELATED APPLICATIONS

This application is a U.S. National Stage Filing under 35 U.S.C. 371 from international Application No. PCT/US2014/058312, filed 30 Sep. 2014, and published as WO 2015/048745 on 2 Apr. 2015, which claims the benefit of the filing date of U.S. application Ser. No. 61/884,697, filed on Sep. 30, 2013, the disclosure of which is incorporated by reference herein.

BACKGROUND

Incontinent individuals or infants can use an absorbent garment, such as a diaper, that is capable of absorbing or containing human waste products. Diapers can have various shapes and sizes, and are generally configured to be worn between an individual's legs and fastened about the waist. Some diapers are reusable and include a washable woven cloth material that can be worn in combination with a fluid-impervious outer garment. Some diapers are disposable and are intended to be discarded after a single use. Such diapers can be configured with a fluid-impermeable or fluid-impervious outer layer (back sheet) and an absorbent inner portion (core).

In some examples, fastening devices can be provided on a front or rear panel of a diaper to secure the diaper about the waist of a wearer. Fastening devices, among other characteristics of a wearable absorbent article, can contribute to a wearer's perception of how well the article fits the wearer, and of how well the article functions.

Some diapers are configured like traditional cloth underwear products and include an elastic waistband instead of, or in addition to, one or more fasteners. Such underwear or brief-style diapers can have front and back panels that are permanently joined together at the sides or hips of the wearer. In an example, the front and back panels can be coupled using an ultrasonic weld that fuses the side edges together. Such diapers are configured to be drawn up over the wearer's legs when the wearer puts on the diaper. These diapers can include absorbent members that are positioned between the wearer's legs and are configured to absorb body fluids.

OVERVIEW

The present inventors have recognized, among other things, that a problem to be solved includes providing a wearable absorbent article that is discrete and has minimally noticeable seams or little bulkiness. The problem can include providing an absorbent article that maintains close physical contact with a wearer's body, such as when the wearer is engaged in physical activity. The present inventors have further recognized that a problem to be solved can include providing a wearable absorbent article that is efficient to manufacture, with minimal waste or trim to be recycled or disposed as a byproduct of the manufacturing process.

The present subject matter can help provide a solution to these problems, such as by providing an absorbent article that is formed from a substantially cylindrical, or tubular, garment structure, such as can be provided using a three-dimensional (circular) knitting machine, using a mold, or using additive manufacturing. In an example, a segment of a cylindrical garment structure can include two waistband regions at opposite end faces of the garment structure. Each of the waistband regions can correspond to a different one of two nested and oppositely-oriented articles, and each of the articles can be converted into a separate and distinct absorbent underwear assembly or article. Converting the segment of the garment structure into the separate absorbent articles can include cutting a portion of the garment structure, such as along a non-linear path, to provide the two articles. Each article includes a waistband region and a body panel region. For each article, opposite end faces of the body panel region can be joined to each other, or joined using an absorbent assembly as a bridge, to provide a substantially seamless underwear garment with an absorbent core.

In an example, the waistband region can be formed continuously with the body panel region of an article, such as using the same material and/or manufacturing technique. For example, a waistband region can include a knit material having a first pattern and a first stretch characteristic, and a body panel region coupled to, and optionally continuous with, the waistband region can include the same knit material having a different second pattern and a different second stretch characteristic.

This overview is intended to provide non-limiting examples of the present subject matter, and this overview is not intended to provide an exclusive or exhaustive explanation. The detailed description below is included to provide further information about the present disposable absorbent articles and related methods.

BRIEF DESCRIPTION OF THE DRAWINGS

In the drawings, which are not necessarily drawn to scale, like numerals may describe similar components in different views. The drawings illustrate generally, by way of example, but not by way of limitation, various embodiments discussed in the present document.

DETAILED DESCRIPTION

Figure 1:
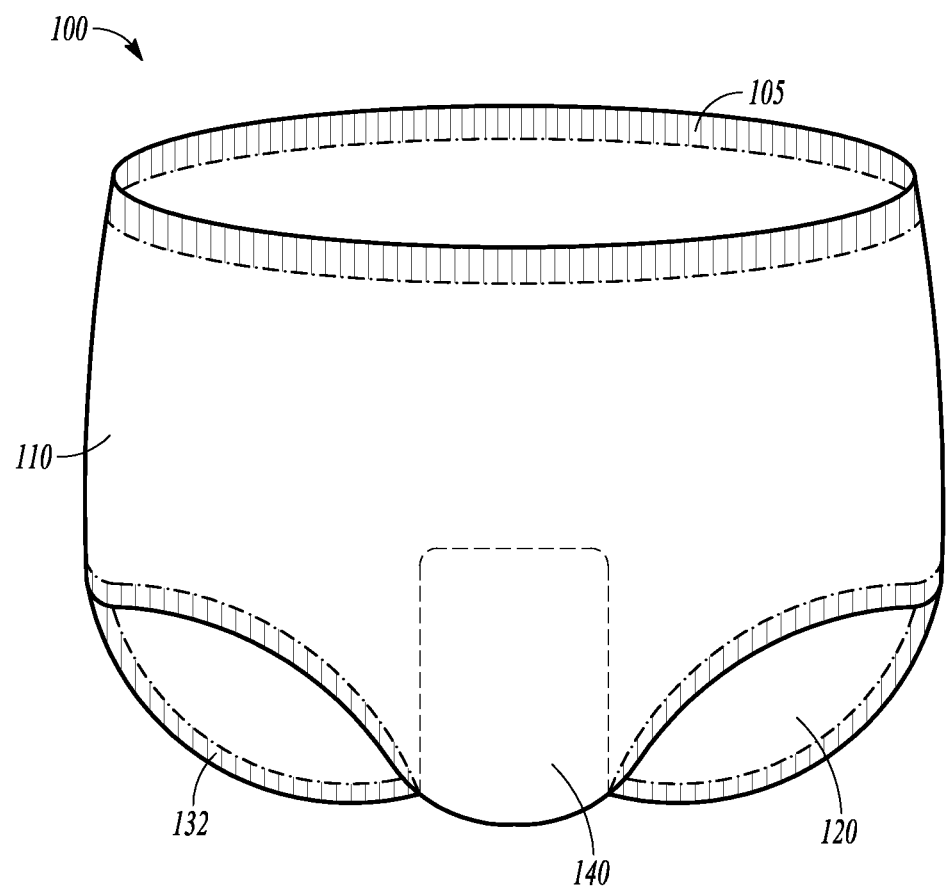
FIG. 1 illustrates generally a front view of an example of a substantially seamless disposable absorbent garment.

This detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. The present inventors also contemplate examples using any combination or permutation of the elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Wearable, disposable absorbent garments that are similar in size, shape, and appearance to cloth undergarments are disclosed herein. A garment, or article, includes at least a waist opening and two leg openings. The garment includes one or more materials that are stretchable, or extensible and retractable, such that the article can elastically conform to different body shapes and sizes. The garment includes an absorbent portion that is configured to be disposed in a wearer's crotch region and to absorb fluids. In an example, a wearable, disposable absorbent garment can include one or more portions that are seamless at one or more locations where a traditional underwear garment would have one or more seams or material junctions.

Individuals who use absorbent garments can have a limited selection of sizes available when choosing an absorbent garment product. Manufacturers of such products have introduced combination sizes, like S/M (small/medium) in order to reduce a number of different products or SKUs for retailers to carry. To combine sizes in this manner, many products use some type of expandable and retractable, or elastic, material to create a product that can accommodate many different sizes of individuals. Due to this combined sizing scheme, a consumer may need to purchase an entire package of a specific product in order to try a product to determine which size provides the best fit.

Improperly-fit absorbent garments can lead to a number of different issues for the wearer of the garment. For example, an improperly-fit garment can be uncomfortable, can adversely affect the wearer's mobility (actual or perceived), and there can be an increased chance of leakage.

A solution to these and other problems can include a disposable garment having an absorbent core and one or more portions made from a seamless, or substantially seamless, stretchable material. In an example, a seamless garment includes an underwear garment that is seamless at its side panels. The garment can be comfortable and can provide users with better sizing options, while still providing a manageable number of SKUs for retailers.

Seamless garments can be preferred for their discreteness, comfort, and non-binding, non-restrictive characteristics. Seamless garments generally show few, if any, lines when worn under tightly fitting clothes. With no seams, seamless garments generally do not fail at areas where traditional cloth garments fail, such as at side seams, fasteners, waistband areas, or other areas traditionally including a seam that can break, fray, or otherwise fail. In an example, a seamless disposable garment can be virtually indistinguishable from a traditional cloth garment when it is worn, such as in terms of the user's perception, and in terms of its outward appearance when worn under clothes.

In an example, a seamless garment comprises a seamless fabric, such as can be manufactured using a circular or three-dimensional knitting machine. Such machines can produce substantially cylindrical, or tubular, seamless garment structures using one or more materials that can be cut or bonded in various configurations to produce clothing and other wearable garments. Generally, any flexible filament or thread-based raw material can be used by a three-dimensional knitting machine to produce a tubular garment structure. Some materials suitable for use by a three-dimensional knitting machine include natural fibers, such as cotton, or synthetic fibers, such as polyester, acetate or triacetate fibers, acrylic or modacrylic fibers, spandex fibers (segmented polyurethanes), anidex fibers (cross linked polyacrylates), elastoester fibers, nylon, or rayon, among others. Some materials used in three-dimensional knitting processes can be bonded using heat, steam, ultrasonic welding, adhesive, traditional sewing or stitching, or other techniques. In an example, a tubular garment structure can be bonded (e.g., to a similar or different material) using a flat stitch to minimize an appearance or feel of a seam.

In an example, a stretchable seamless fabric can be produced as a continuous tube of material with an open end face opposite the production apparatus, such as a three-dimensional knitting machine. The tube of material can be made according to specified width (or diameter) and height (or length) characteristics. In an example, one or more characteristics of the tube can be updated or changed in the course of a build process. For example, a first portion of the tube can be made to have a first tube width, and a subsequent second portion that is continuous with the first portion can be made to have a different second tube width. The tube of material can be cut, such as to remove a portion of the tube material from the machine that produced the continuous tube. At least a portion of one of the open ends of the tube can be joined, such as to a different assembly or to an opposite side of the tube material itself, to provide a panel portion that is configured to be worn between the legs. An absorbent core can be positioned at or near the joined portion and can be configured to be positioned in the crotch area of a wearer.

In an example, a seamless disposable garment provides maximum flexibility by way of the fabric comprising the garment. The seamless garment can stretch or expand in multiple directions to accommodate a wide range of waist or torso shapes and sizes. In some examples, differently sized garments can be made using differently sized seamless material tubes (i.e., tubes having different widths, or diameters). In some examples, a stretch characteristic of a seamless garment can be influenced by a weave or knit pattern that is used to construct the garment tube.

FIG. 1 illustrates generally an example of a front view of a disposable absorbent article 100. The absorbent article 100 can be configured to be similar in size, shape, and appearance to a traditional cloth undergarment, and can be configured or designed for use by men or by women. The absorbent article 100 can include, from top to bottom, a waistband region 105, a substantially tubular or cylindrical body panel portion, and a crotch portion that is configured to extend between a user's legs. The body panel portion includes a front panel 110 configured to be worn at the user's front side, and a rear panel 120 configured to be worn at the user's rear or back side. The crotch portion includes an absorbent assembly 140, such as including a pulp, fluff, composite fiber, super-absorbent polymer, air-laid material, or one or more other materials or a combination of materials that is configured to absorb liquid.

The absorbent article 100 includes a leg hole on each side of the absorbent assembly 140. A leg cuff 132 can be provided or formed around all or a portion of a perimeter of each of the leg holes. The leg cuff 132 can optionally include an elastic material that extends substantially around each of a wearer's legs to provide a seal that can prevent leakage. The leg cuff 132 can additionally or alternatively include a rounded or tapered edge to improve comfort.

In an example, the substantially tubular or cylindrical body panel portion of the absorbent article 100 includes a continuous, seamless tube of material that is manufactured using a three-dimensional or circular knitting process or machine. The crotch portion can optionally be formed from the same continuous material as the body panel portion. For example, edges of an open end of the body panel portion can be joined to form the crotch portion. The leg holes can be provided at the sides of the crotch portion, such as by cutting, stitching, or otherwise bonding the continuous, seamless tube of material.

The waistband region 105 can optionally be integrally formed with the body panel portion of the absorbent article 100. That is, the waistband region 105 can be made from the same material as the material used in the body panel portion, such as using the same knitting process or machine. In an example, the waistband region 105 can have a different texture, stitch or weave pattern, density, or stretch characteristic than the body portion of the absorbent article 100.

The waistband region 105 can be seamless or can be made from a substantially linear strip of stretchable material, such as can be joined at one or more locations to form a substantially circular waistband. In an example, the waistband region 105 includes one or more elastic strands, an elastomeric film, or one or more other extensible and retractable materials. In an example where the waistband region 105 is not integrally formed with a corresponding body panel portion, the waistband region 105 can be connected to a top edge or end region of a body panel, such as using conventional stitching, bonding, or other adhesive means.

In an example, the absorbent assembly 140 can be used to join the front panel 110 and the rear panel 120 of the absorbent article 100. In another example, the front panel 110 and the rear panel 120 are directly coupled or joined together, and the absorbent assembly 140 can be coupled to or positioned over the junction between the front panel 110 and the rear panel 120. In the example of FIG. 1, the absorbent assembly 140 includes end portions that are coupled to the front and rear panels 110 and 120.

Figure 2:
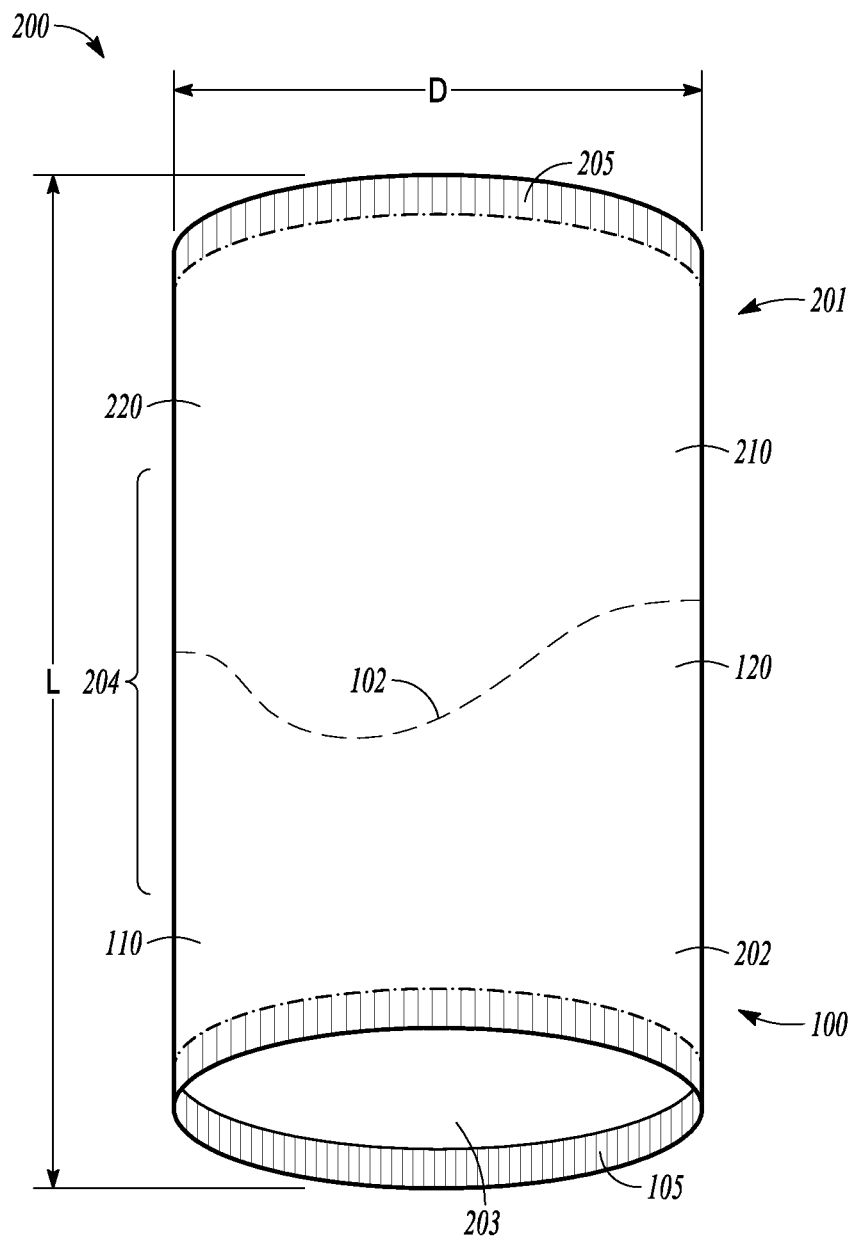
FIG. 2 illustrates generally a perspective view of an example of a substantially cylindrical and seamless garment structure.

FIG. 2 illustrates generally an example of a perspective view of a portion of a substantially cylindrical garment structure 200. The garment structure 200 can be used to provide two different absorbent articles with little or no trim or waste material byproducts. The garment structure 200 can be formed from a flexible synthetic or natural stranded material using a three-dimensional knitting machine, using an additive manufacturing machine (e.g., using a three-dimensional printer), or using a mold.

As shown in the example of FIG. 2, the garment structure 200 has a diameter D and a length L. In a relaxed or unstretched state, the diameter of the garment structure 200 corresponds to a minimum waistband size of an absorbent article. The length of the garment structure 200 corresponds to a vertical size or height of an absorbent article. For example, a lesser length or height can correspond to a low-rise or bikini-style absorbent article, whereas a greater length or height can correspond to a high cut, or brief-style absorbent article.

The garment structure 200 has open end faces corresponding to respective first and second waistband regions 105 and 205. The garment structure 200 includes a continuous central region 204 that extends between the first and second waistband regions 105 and 205. The central region 204 is substantially cylindrical and includes an outer facing surface 202 and an inner facing surface 203. In an example, such as shown in the example of FIG. 2, the inner and outer facing surfaces 202 and 203 are continuous, unbroken surfaces that can include one or more patterns, designs, or other features, such as can be woven into or printed on the garment structure 200. In an example, size indicia can be included on one of the inner facing surface 203 and the outer facing surface 202 of each article, such as near a waistband region. In an example, size indicia can be included on the outer facing surface 202 of the garment structure 200, and the garment structure 200 can be turned inside-out during the article conversion process, such that the size indicia is included at the inside surface of the completed absorbent article.

In the example of FIG. 2, a first absorbent article 100 (e.g., corresponding to the absorbent article 100 of FIG. 1) is shown in a first orientation. The first absorbent article 100 includes the first waistband region 105, a first front panel 110, and a first rear panel 120. At least the first front panel 110 and the first rear panel 120 are portions of the garment structure 200. Optionally, the first waistband region 105 is formed from the same material as the central region 204 of the garment structure 200. In an example, the first waistband region 105 is formed from a different material than the central region 204. For example, a knitting machine used to produce the first waistband region 105 and the central region 204 can receive different threads at different times to create the first waistband region 105 and the central region 204 using different thread materials. In the garment structure 200, the panel portions of the first absorbent article 100 can be continuous with panel portions of a second absorbent article 201. As shown in the example of FIG. 2, the second absorbent article 201 includes the second waistband region 205, a second front panel 210, and a second rear panel 220.

The first and second absorbent articles 100 and 201 can be separated along a cut line 102 in the central region 204 of the garment structure 200. As shown in the example of FIG. 2, the cut line 102 can be non-linear, such as to provide a contoured shape to the final absorbent article. A linear cut line can alternatively be used. The first and second absorbent articles 100 and 201 can be separated by cutting the garment structure 200 using a knife, water jet, laser, or other means to sever the fibers, linked polymers, or other material of the garment structure 200. In an example, the articles can be separated using heat. In an example, the density, texture, or weave pattern of the garment structure 200 at or near the cut line 102 can be different than the density, texture, or weave pattern used elsewhere in the garment structure 200 to facilitate separating the articles. For example, a more or less dense weave pattern can be used at the cut line 102 than is used elsewhere in the garment structure 200.

In an example, after separating the first and second absorbent articles 100 and 201 at the cut line 102, the cut edges (opposite the first and second waist band regions 105 and 205, respectively) can be treated to prevent the garment structure 200 material from fraying, disentangling, or otherwise unraveling at the newly cut edges. The material itself can be treated, such as using heat, ultrasonic energy, or hammering, among other techniques. In an example, one or more other materials can be adhered or coupled to the cut edges, such as to provide a portion of a leg cuff region in the assembled absorbent article.

In FIG. 2, the rear panels of the illustrated first and second absorbent articles 100 and 201 have a greater length than the illustrated front panels. As shown in FIG. 2, the first and second absorbent articles 100 and 201 are nested, that is, they are oriented along the garment structure 200 at 180 degrees relative to one another. For example, in the central region 204 of the garment structure 200, the first front panel 110 of the first absorbent article 100 is adjacent the second rear panel 220 of the second absorbent article 201, and the first rear panel 120 of the first absorbent article 100 is adjacent the second front panel 210 of the second absorbent article 201. Although other configurations or orientations of the first and second absorbent articles 100 and 201 can be used, the configuration shown in FIG. 2 efficiently provides a contoured absorbent article and minimizes waste in the conversion process.

In the example of FIG. 2, the garment structure 200 is shown including the first and second waistband regions 105 and 205. Optionally, the first and second waistband regions 105 and 205 can be prepared or coupled to the first and second absorbent articles 100 and 201 after the articles are separated at the cut line 102.

Figure 3A:
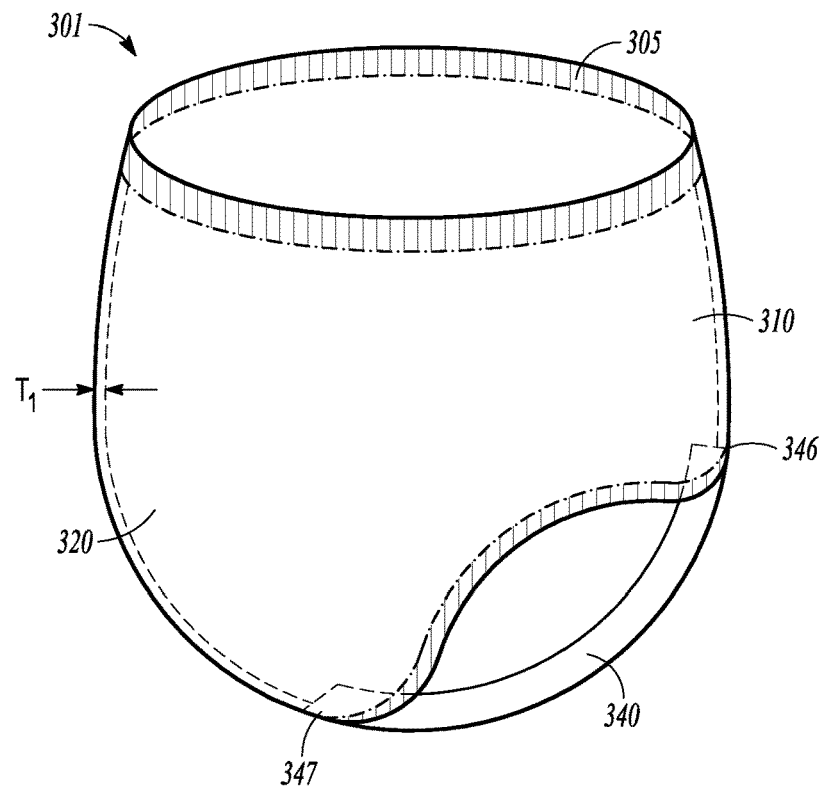
FIG. 3A illustrates generally a side view of an example of a first absorbent article.
Figure 3B:
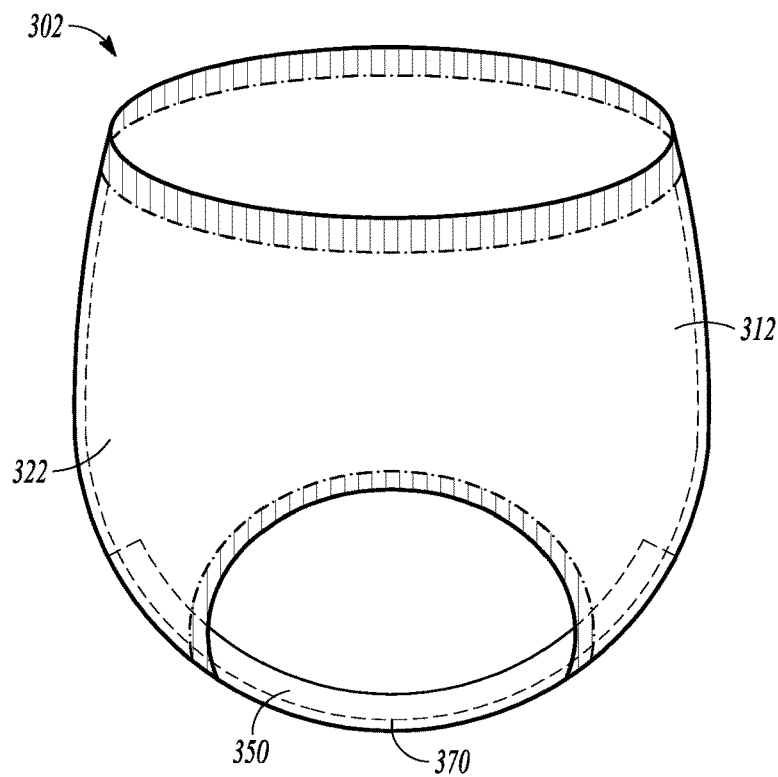
FIG. 3B illustrates generally a side view of an example of a second absorbent article.

After separating the first and second absorbent articles 100 and 201, an absorbent assembly can be coupled with or inserted into each of the articles. FIGS. 3A and 3B illustrate generally side views of different first and second absorbent articles 301 and 302 having different configurations. In the first article 301, in FIG. 3A, a first absorbent assembly 340 bridges a gap between a front panel 310 and a rear panel 320 of the absorbent article. Leg holes are provided on opposite longitudinal sides of the first absorbent assembly 340, and a first waistband 305 is provided opposite the leg holes.

In the example of FIG. 3A, the first absorbent assembly 340 includes front and rear portions 346 and 347 that are coupled to the front panel 310 and the rear panel 320, respectively. The front portion 346 of the first absorbent assembly 340 overlays and is adhered to the front panel 310, and the rear portion 347 of the first absorbent assembly 340 overlays and is adhered to the rear panel 320. In an example, only side edge portions of the first absorbent assembly 340 are coupled to the front panel 310 and the rear panel 320, such as using flat stitching or other coupling means, without the overlay portions.

Figure 4A:
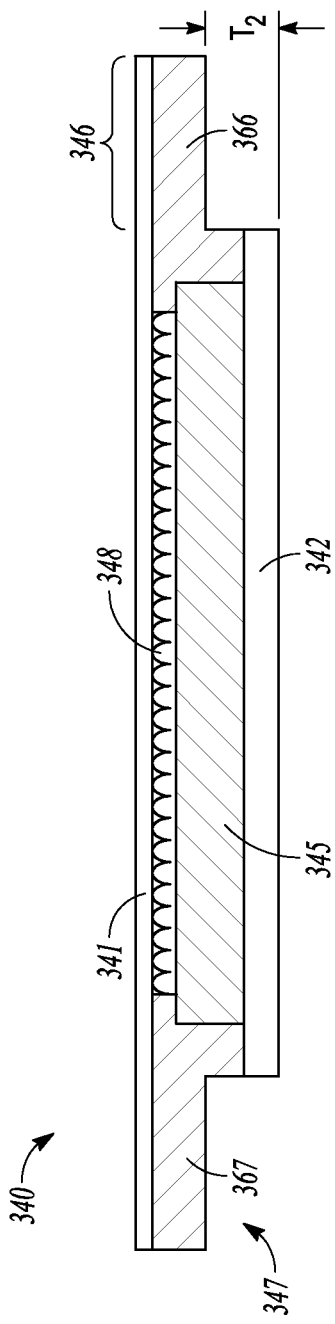
FIG. 4A illustrates generally a cross-section view of an example of a first absorbent assembly.

FIG. 4A illustrates generally a central, cross section view of the first absorbent assembly 340 in a flattened configuration. From top to bottom, the first absorbent assembly 340 can include one or more of a liquid-permeable topsheet 341, an acquisition-distribution layer 348, an absorbent core 345, and a liquid-impervious backsheet 342. The absorbent core 345 is configured to absorb a liquid, and can include one or more of a pulp, fluff, composite fiber, super-absorbent polymer, air-laid material, or one or more other materials. The liquid-impervious backsheet 342 can include a polymer film, a non-woven cloth, a laminate, or other substantially liquid-impervious material.

In an example, the front and rear portions 346 and 347 of the first absorbent assembly 340 do not include at least a portion of the absorbent core 345. The thickness of the first absorbent assembly 340 at the front and rear portions 346 and 347 can therefore be less than the thickness of the first absorbent assembly 340 at a central portion of the assembly. A thickness $T_2$, corresponding to the difference in thickness between the central portion and the front and/or rear portions 346 and 347, can be approximately the same as a thickness $T_1$ (see FIG. 3A) of the garment structure used to make the front and/or rear panels 310 and 320. When the thicknesses $T_1$ and $T_2$ are sufficiently similar, the outward facing side of the absorbent article can appear to be substantially seamless or flat.

The first absorbent assembly 340 can optionally include connective portions 366 and 367 that are positioned adjacent to the ends of the absorbent core 345. The connective portions 366 and 367 can be configured to facilitate coupling the first absorbent assembly 340 to the front and rear panels 310 and 320 of an absorbent article. In an example, the connective portions 366 and 367 can be liquid impervious, such as to inhibit or prevent the garment material in the front and rear panels 310 and 320 from wicking moisture from the absorbent core 345 when the first absorbent assembly 340 is coupled with the front and rear panels 310 and 320.

The absorbent assembly 340 can have various shapes, densities, or configurations. For example, the absorbent assembly 340 can include an absorbent portion that is disposed only at or near the front side or the rear side of the absorbent article. In an example, the absorbent assembly includes an elongated hourglass shape that is configured to provide absorbent material in waste source areas in front of and behind the wearer, and to minimize an amount of absorbent material disposed between the wearer's legs when the garment is worn.

Figure 5:
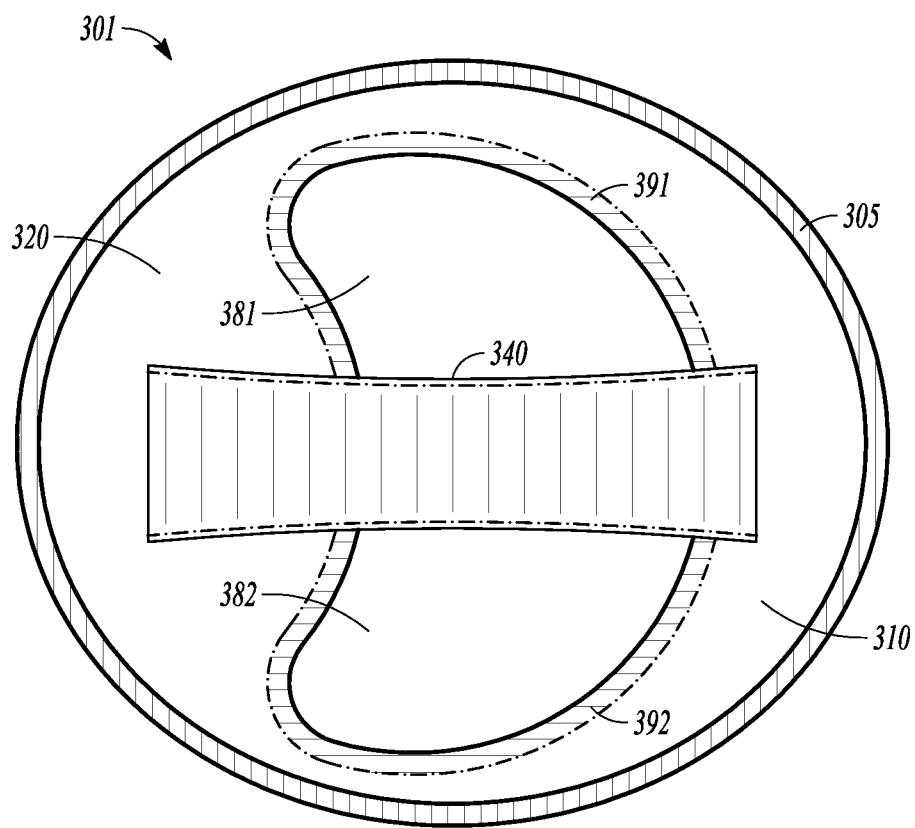
FIG. 5 illustrates generally a top view of an example of the first absorbent article of FIG. 3A.

FIG. 5 illustrates generally a top view of the first absorbent article 301. In this view, the first absorbent assembly 340 can be seen to be attached to the front panel 310 and the rear panel 320, with a left leg opening 381 and a right leg opening 382 on opposite longitudinal sides of the absorbent assembly 340. Left and right leg cuffs 391 and 392 can be provided around the respective perimeter edges of the left and right leg openings 381 and 382. The leg cuffs 391 and 392 can include an extensible and retractable material that is configured to abut and substantially surround each of the wearer's legs to provide an actual or perceived liquid barrier.

Referring now to the second absorbent article 302, in FIG. 3B, a bottom edge of a second front panel 312 is joined with a bottom edge of a second rear panel 322 at a junction 370. The junction 370 is a location where a bottom edge portion of the front panel 312 is coupled or secured to a bottom edge portion of the rear panel 322, such as using flat stitching, ultrasonic bonding, or other means. In an example, one of the front panel 312 and the rear panel 322 can overlap the other at the junction 370. Leg holes are provided on opposite sides of the junction 370 to form the second absorbent article 302. The junction 370 can be formed using flat stitching, heat, ultrasonic bonding, adhesive, or other means to join the second front panel 312 and the second rear panel 322. In the example of FIG. 3B, a second absorbent assembly 350 is coupled to the second absorbent article 302 in a crotch region, and the crotch region can include the junction 370.

Figure 4B:
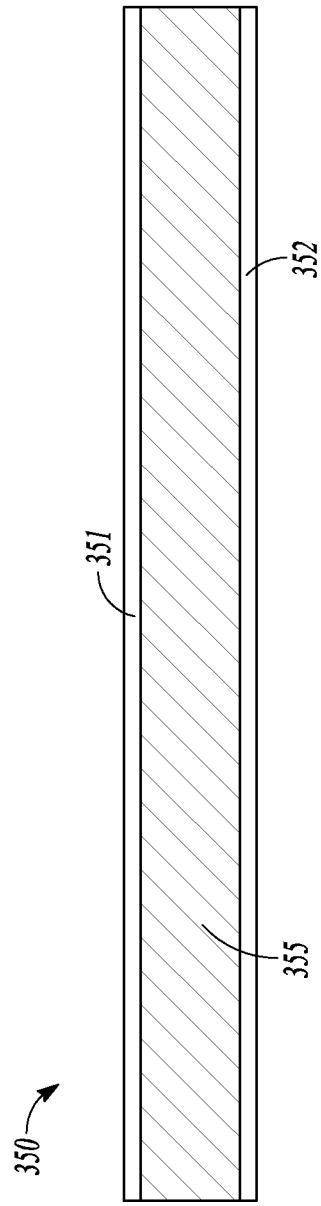
FIG. 4B illustrates generally a cross-section view of an example of a second absorbent assembly.

FIG. 4B illustrates generally a central, cross section view of the second absorbent assembly 350 in a flattened configuration. From top to bottom, the second absorbent assembly 350 can include one or more of a liquid-permeable topsheet 351, an acquisition-distribution layer (not shown), an absorbent core 355, and a liquid-impervious backsheet 352. In an example, the second absorbent assembly 350 can include tapered ends or sides (not shown) to improve comfort or appearance.

Figure 6:
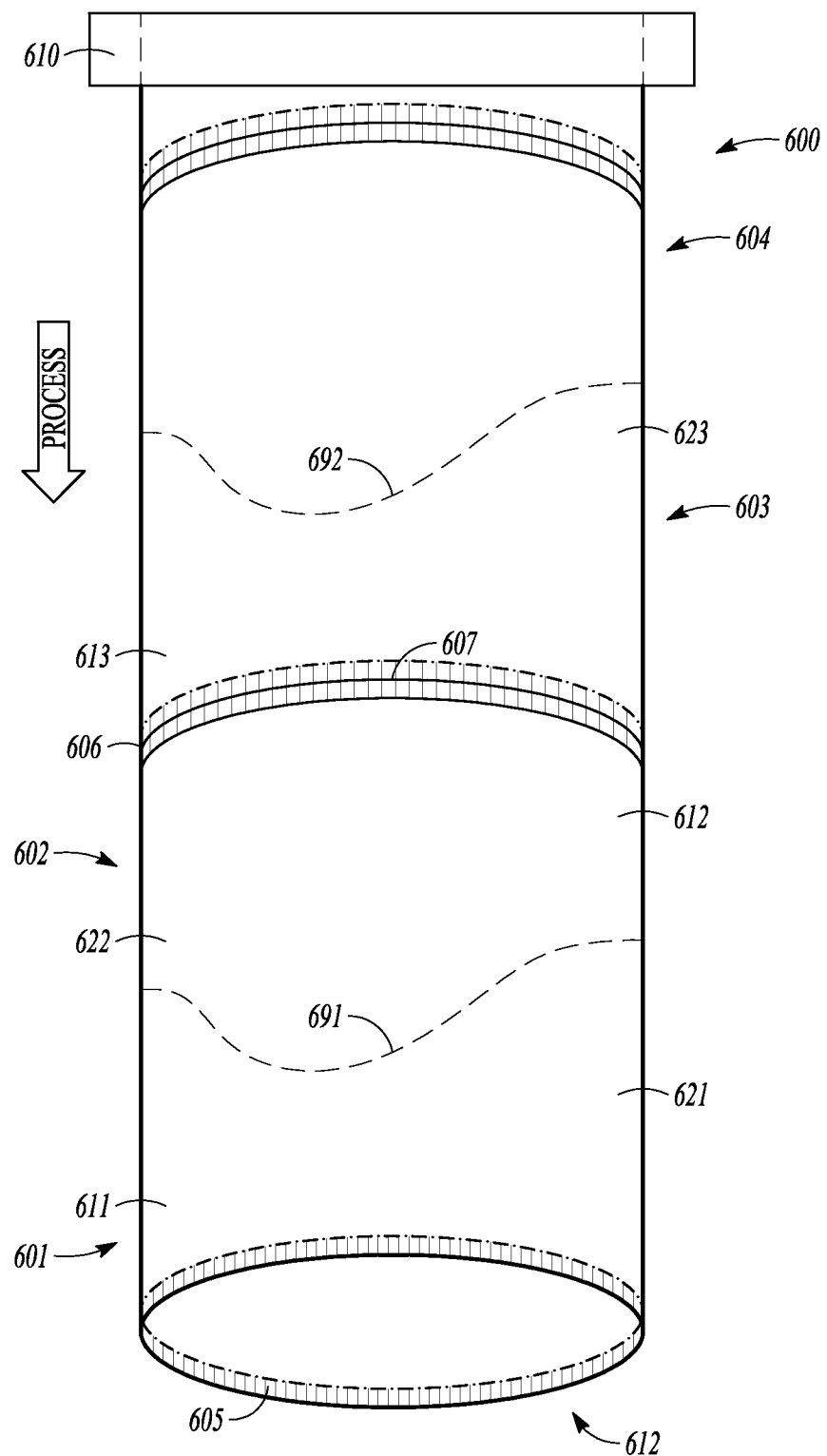
FIG. 6 illustrates generally a perspective view of an example of a substantially cylindrical seamless garment structure and a knitting machine.

Referring now to FIG. 6, an example illustrates generally a cylindrical garment structure 600 produced by a three-dimensional knitting machine 610. The knitting machine 610 can be configured to continuously produce the garment structure 600, and various garment portions or articles can be intermittently or periodically cut and removed from the garment structure 600 as it is produced. As indicated in FIG. 6, a process direction can proceed from the knitting machine 610 to an open garment end 612 of the garment structure 600.

The garment structure 600 can be a continuous woven fabric having a uniform weave pattern, or the garment structure 600 can include one or more features or different patterns woven into the fabric at various specified locations. In the example of FIG. 6, the garment structure 600 includes multiple waistband features that are disposed at regular intervals along the length of the structure. The multiple waistband features can correspond to different absorbent articles that can be separated from the continuous garment structure 600.

In the example of FIG. 6, the open garment end 612 of the garment structure 600 includes a first waistband region 605 of a first article 601. The first article 601 includes front and rear panels 611 and 621, such as can have configurations similar to the front and rear panels described above in the examples of FIG. 3A or 3B. The first article 601 can be adjacent a second article 602 in the garment structure 600. The second article 602 can include respective front and rear panels 612 and 622. The first and second articles 601 and 602 can be separated along a first cut line 691, such as similarly described above in the example of FIG. 2 at the cut line 102.

After the first article 601 is separated from the second article 602 at the first cut line 691, the first article 601 can proceed to one or more downstream processes, such as including (1) applying an absorbent assembly between the front and rear panels 611 and 621 of the first article 601 (see, e.g., FIG. 3A), or (2) joining the front and rear panels 611 and 621 (see, e.g., FIG. 3B).

In the example of FIG. 6, the first and second articles 601 and 602 are continuous throughout their respective body portions before the articles are separated. The second article 602 includes a second waistband 606 at an end of the second article 602 that is opposite the first article 601. A third waistband 607 can be formed continuously with the second waistband 606. After a sufficient amount of the third waistband 607 is prepared by the knitting machine 610, the second and third waistbands 606 and 607 can be separated, such as using the same or different means used to separate the first and second articles 601 and 602 at the first cut line 691. After the second article 602 is separated from the third waistband 607, the second article 602 can proceed to one or more downstream processes. In an example, one or both of the second and third waistbands 606 and 607 can be treated or sealed when the second and third articles 602 and 603 are separated to inhibit any waistband material from unraveling.

The third waistband 607 can be formed by the knitting machine 610 continuously with third front and rear body panels 613 and 623 of a third article 603. A fourth article 604 can be formed adjacent to and continuous with the third article 603, such as in the same or similar manner to that described above for the first and second articles 601 and 602. The knitting machine 610 can thereby produce a continuous web of three-dimensional garment material that can be periodically or intermittently cut to separate individual garment units from the continuous web.

Figure 7:
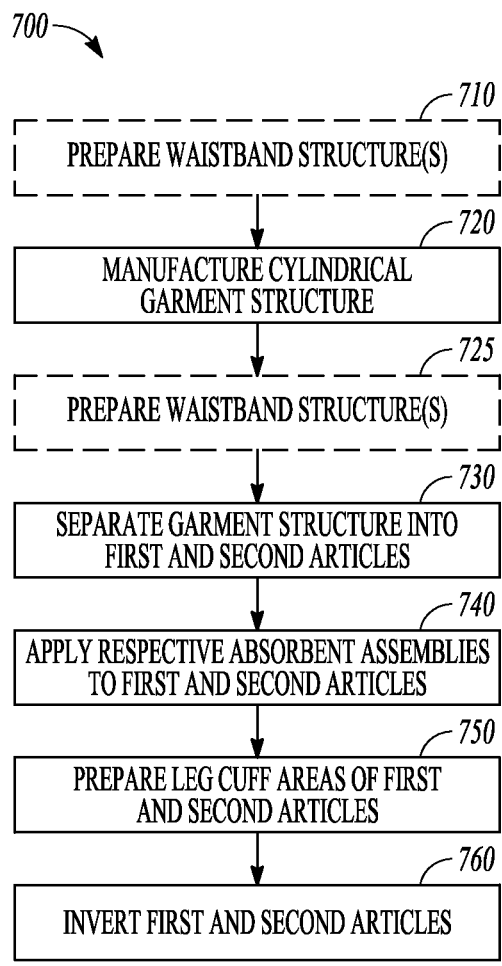
FIG. 7 illustrates generally an example of a method that includes preparing an absorbent article using a substantially cylindrical garment structure.
Figure 8:
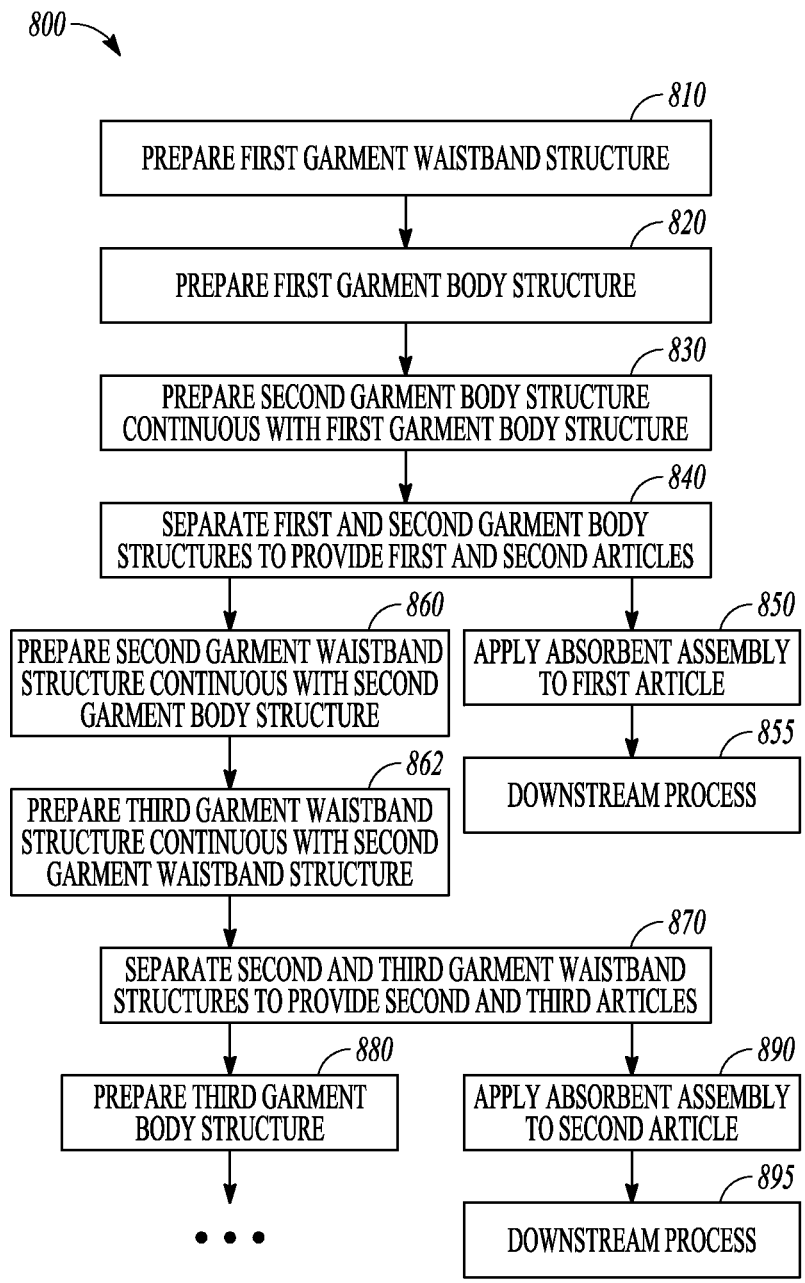
FIG. 8 illustrates generally an example of a method that includes preparing absorbent articles using a continuous garment structure.

FIGS. 7 and 8 illustrate generally examples of methods that can be applied to produce one or more substantially seamless absorbent articles. FIG. 7 illustrates generally an example 700 that includes preparing an absorbent article using a substantially cylindrical garment structure. At 710, the method can optionally include preparing one or more waistband structures. Multiple waistband structures can be prepared, such as in advance or in parallel with preparing one or more corresponding absorbent article body portions. Multiple waistband structures can optionally be prepared as a continuous cylindrical structure using a three-dimensional knitting machine, and the multiple waistband structures can be cut or separated to form discrete waistband structures. A weave style, pattern, material type, or diameter of the structures can be specified according to a desired size of an absorbent article to be manufactured.

At 720, the example 700 includes manufacturing a cylindrical garment structure that is configured for use as a body portion of an absorbent garment. For example, at 720, the method can include manufacturing the central region 204 of the garment structure 200 illustrated in FIG. 2. The cylindrical garment structure manufactured at 720 can have a substantially smooth, continuous, and contiguous surface, or the structure can be textured, patterned, or can include one or more voids or other features according to a specified design.

At 725, the example 700 can include preparing a waistband structure, such as in-line or continuous with the cylindrical garment structure that was manufactured at 720. In an example that includes the waistband structure prepared at 710, the step at 725 can include attaching the earlier-prepared waistband structure to the garment structure that was prepared at 720.

In an example, preparing the waistband structure at 725 can correspond to preparing the second waistband region 205 in the example of FIG. 2. That is, at 725, the method can include changing a knitting machine from preparing a body panel weave or style, such as for the body panels of the second absorbent article 201, to preparing a waistband weave or style for the second waistband 205.

At 730, the method 700 can include separating a garment structure to form multiple absorbent articles. With reference to FIGS. 2 and 7, for example, separating a garment structure at 730 can include separating or cutting the garment structure 200, such as along the cut line 102, to separate the first absorbent article 100 and the second absorbent article 201. Separating the garment structure at 730 can include using a knife, blade, scissors, water jet, or other cutting tool to sever one or more threads or other materials comprising the central region 204 of the garment structure 200.

At 740, the method 700 includes applying respective absorbent assemblies to the first and second absorbent articles that were separated at 730. Applying an absorbent assembly, for example, can include adhering a portion of a backsheet of an absorbent assembly to an outer facing surface of the body panels of the first absorbent article. In this configuration, the absorbent article with the absorbent assembly attached is inside-out. The absorbent article can be turned right-side out prior to packaging or further processing. Optionally, the absorbent article can be inverted or turned right-side out prior to applying the absorbent assembly to the body panels.

Applying an absorbent assembly can include adhering a portion of a backsheet of an absorbent assembly to an inner facing surface of the body panels of the first absorbent article. In this configuration, the absorbent article with the absorbent assembly attached is right-side out and ready for further processing, such as folding or packaging.

At 750, the method 700 includes preparing leg cuff areas of the first and second articles, such as after the absorbent assemblies are attached to the respective absorbent articles. Preparing the leg cuff areas can include bonding an elastic material at or around the leg opening areas of each of the absorbent articles. In an example, preparing the leg cuff areas at 750 includes capping, sealing, or otherwise terminating the open end perimeter of the body portions at the leg openings to prevent the body panel material from unraveling.

At 760, the method 700 includes inverting the first and second articles to turn the articles from an inside-out configuration to a right-side out configuration for packaging or use. Thus, when a user selects one of the first or second articles, the selected article is configured to be easily pulled up over the legs and secured about the user's waist.

FIG. 8 illustrates generally an example 800 of a method that can include preparing multiple absorbent articles from a substantially continuous source of cylindrical garment material, such as can be provided using a continuous three-dimensional knitting machine. The following discussion of FIG. 8 includes, for illustration only, non-limiting references to the diagram of the garment structure 600 included at FIG. 6.

At 810, the method includes preparing a first garment waistband structure. For example, preparing the first garment waistband structure at 810 can include using the knitting machine 610 to prepare the first waistband region 605 having a first knit pattern. At 820, the method includes preparing a first garment body structure. Preparing the first garment body structure can include preparing the front panel 611 and rear panel 621 of the first article 601, such as using the same first knit pattern or a different second knit pattern.

At 830, the method includes preparing a second garment body structure. Preparing the second garment body structure can include preparing all or a portion of the front panel 612 and the rear panel 622 of the second absorbent article. Preparing the first and second garment body structures at 820 and 830 can include using the same or different material, weave pattern, or other characteristic of the structures.

At 840, the method includes separating the first and second garment body structures, such as prepared at 820 and 830, to provide first and second articles. In the example of FIG. 6, for example, the first and second articles 601 and 602 can be separated at the first cut line 691 to separate the first article 601 from the second article 602, such as when the second article 602 remains in-process or otherwise remains connected to the knitting machine 610.

After step 840, the first article 601 is detached from the continuous garment structure being produced by the knitting machine 610, and the first article 601 can receive further processing. For example, at 850, the example can include applying an absorbent assembly to the first article 601. The absorbent assembly can be applied, attached, or otherwise coupled to the first article 601, such as described herein at FIG. 3A or 3B. At 855, one or more additional downstream processes can be applied to the first article 601, including inverting the first article 601 (see, e.g., FIG. 7 at 760), preparing a leg cuff, applying a label or other indicia, or preparing the first article 601 for packaging or shipment, including folding the first article 601 using an automated folding machine.

After step 840, the second article 602 can remain attached to the continuous garment structure being produced by the knitting machine 610. At 860, any remaining portion of a body portion of the second article 602 can be prepared by the knitting machine 610. At 860, a second garment waistband structure can be prepared, such as continuously with the second garment body structure. In an example, the second garment waistband structure can have a similar or dissimilar construction as compared to the first garment waistband structure prepared at 810 for the first garment.

At 862, the knitting machine 610 can prepare a third garment waistband structure, such as continuously with the second garment waistband structure. At 870, such as after a sufficient amount of the third garment waistband structure is prepared by the knitting machine 610, the second and third garment waistband structures can be separated to provide second and third articles, such as corresponding to the second article 602 and the third article 603 in the example of FIG. 6.

After step 870, the second article 602 is detached from the continuous garment structure being produced by the knitting machine 610, and the second article 602 can receive further processing. For example, at 890, the example can include applying an absorbent assembly to the second article 602. The absorbent assembly can be applied, attached, or otherwise coupled to the second article 602, such as described herein at FIGS. 3A and 3B. At 895, one or more additional downstream processes can be applied to the second article 602, including inverting the second article 602 (see, e.g., FIG. 7 at 760), preparing a leg cuff, applying a label or other indicia, or preparing the second article 602 for packaging or shipment, including folding the second article 602 using an automated folding machine. After step 870, the third article 603 can remain attached to the knitting machine 610, and the example can proceed at 880 with using the knitting machine 610 to prepare a third garment body structure.

The example of FIG. 8 can be substantially repeated, in whole or in part, to provide a continuous stream of articles that can be configured for use as absorbent underwear products. One or more characteristics of the equipment, material, or process can be adjusted to provide absorbent articles having different characteristics. For example, different raw materials can be used for different articles, or a diameter of the garment structure or waistband can be changed to produce articles that are differently sized or styled. Although the preceding examples are generally described as using a garment structure produced using a three-dimensional knitting machine, other types of automated machines can be used. For example, a substantially cylindrical garment structure can be printed using additive manufacturing or deposition techniques, or the substantially cylindrical garment structure can be molded, such as using a blown material or film. In an example, a cylindrical garment structure can be prepared using a spray system that is configured to dispense polymer materials that can harden with exposure to light or air, such as including Fabrican spray-on fabric and the like.

To further illustrate the articles and methods disclosed herein, several non-limiting examples are provided below.

Example 1 can include or use subject matter such as an apparatus, or a method of making an apparatus, such as can include or use a disposable absorbent garment. In Example 1, the disposable absorbent garment can comprise or use, among other things, a substantially tubular upper portion configured to be worn at or below a wearer's waist, and an absorbent panel portion having an absorbent core configured to correspond to a body fluid insult area when the garment is worn.

Example 2 can include, or can optionally be combined with the subject matter of Example 1, to optionally include the substantially tubular upper portion and the absorbent panel portion, wherein the portions comprise the same contiguous and substantially seamless material.

Example 3 can include, or can optionally be combined with the subject matter of any of Examples 1 or 2 to optionally include the absorbent panel portion comprises joined extensions of the substantially tubular upper portion.

Example 4 can include, or can optionally be combined with the subject matter of Example 3 to optionally include extensions that are joined using heat, adhesive, stitching, or flat stitching.

Example 5 can include, or can optionally be combined with the subject matter of any of Examples 3 or 4 to optionally include one or more leg holes that can be provided at the sides of the joined extensions.

Example 6 can include, or can optionally be combined with the subject matter of any of Examples 2 through 5 to optionally include the substantially tubular upper portion includes an extensible and retractable substantially seamless material.

Example 7 can include, or can optionally be combined with the subject matter of any of Examples 2 through 6 to optionally include the absorbent panel portion comprises an absorbent core configured to absorb and retain fluid.

Example 8 can include, or can optionally be combined with the subject matter of any of Examples 2 through 7 to optionally include the substantially tubular upper portion is sufficiently expandable to accommodate multiple different wearer waist circumferences.

Example 9 can include, or can optionally be combined with the subject matter of any of Examples 1 through 8 to optionally include the substantially tubular upper portion is substantially seamless.

Example 10 can include, or can optionally be combined with the subject matter of any of Examples 1 through 9 to optionally include the substantially tubular upper portion is seamless throughout hip regions of the garment.

Example 11 can include, or can optionally be combined with the subject matter of any of Examples 1 through 10 to optionally include the substantially tubular upper portion is seamless between an upper waistband area and a leg hole opening.

Example 12 can include, or can optionally be combined with the subject matter of any of Examples 1 through 11 to optionally include the substantially tubular upper portion is seamlessly coupled to the absorbent panel portion.

Example 13 can include, or can optionally be combined with the subject matter of any of Examples 1 through 12 to optionally include the substantially tubular upper portion coupled to the absorbent panel portion.

Example 14 can include, or can optionally be combined with the subject matter of one or any combination of Examples 1 through 13 to include, subject matter (such as an apparatus, a method, a means for performing acts, or a machine readable medium including instructions that, when performed by the machine, that can cause the machine to perform acts), such as can include a disposable absorbent garment, comprising a waistband assembly configured to be worn at, near, or about a waist of a subject, or an absorbent panel assembly having first and second ends that are coupled to the waistband assembly, the absorbent panel assembly including a liquid-pervious body-side layer, a liquid impervious external layer, and an absorbent core positioned between the body-side and external layers. In Example 14, the waistband assembly can be substantially seamless. For example, hip regions that would traditionally include one or more vertical seams can be seamless.

Example 15 can include, or can optionally be combined with the subject matter of one or any combination of Examples 1 through 14 to include, subject matter (such as an apparatus, a method, a means for performing acts, or a machine readable medium including instructions that, when performed by the machine, that can cause the machine to perform acts), such as can include a method of manufacturing a disposable absorbent garment, comprising providing a continuous tube of seamless stretchable fabric, or joining at least a portion of one side of one of the open ends of the continuous tube to an opposite side of the same open end to provide leg openings at either side of the joined portion, or applying an absorbent core to an area at or near the joined portion.

Example 16 can include, or can optionally be combined with the subject matter of one or any combination of Examples 1 through 15 to include, subject matter (such as an apparatus, a method, a means for performing acts, or a machine readable medium including instructions that, when performed by the machine, that can cause the machine to perform acts), such as can include a method of manufacturing a disposable absorbent garment, comprising: providing a continuous tube of stretchable fabric, or joining at least a portion of an open end of the continuous tube to an absorbent panel assembly configured to extend between a wearer's legs when the garment is worn.

Example 17 can include, or can optionally be combined with the subject matter of one or any combination of Examples 1 through 16 to include, subject matter (such as an apparatus, a method, a means for performing acts, or a machine readable medium including instructions that, when performed by the machine, that can cause the machine to perform acts), such as can include a method for manufacturing substantially seamless incontinence underwear products, including manufacturing a substantially cylindrical garment structure using a stretchable garment material, the garment structure including first and second open end faces and a substantially cylindrical body portion between the first and second open end faces, the substantially cylindrical body portion of the garment structure including an inner facing surface, and an outer facing surface. In Example 17, such as at or near the perimeter edges of the first and second open end faces, the method can include preparing respective first and second waistband regions, and separating the garment structure into first and second articles at a central region of the body portion, the first article including the first waistband area and substantially a first half of the body portion of the garment structure, and the second article including the second waistband area and substantially a second half of the body portion of the garment structure. Example 17 can include applying respective first and second absorbent assemblies to the first and second articles to provide respective first and second substantially seamless incontinence underwear products.

Example 18 can include, or can optionally be combined with the subject matter of Example 17, to optionally include using a three-dimensional knitting machine to knit all or a portion the garment structure using one or more garment material filaments.

Example 19 can include, or can optionally be combined with the subject matter of any of Examples 17 or 18 to optionally include molding, printing, or depositing all or a portion of the garment structure.

Example 20 can include, or can optionally be combined with the subject matter of any of Examples 17 through 19 to optionally include preparing the first waistband area in a portion of the garment structure that extends from the perimeter edge of the first open end face toward a center of the garment structure, the first waistband area having a different texture, density, or stretch characteristic than the body portion of the garment structure.

Example 21 can include, or can optionally be combined with the subject matter of any of Examples 17 through 20 to optionally include attaching a waistband material at the perimeter edge of the first open end face and extending from the first open end face away from a center of the garment structure, the waistband material having a different texture, density, or stretch characteristic than the body portion of the garment structure.

Example 22 can include, or can optionally be combined with the subject matter of any of Examples 17 through 21 to optionally include separating the garment structure into first and second articles at the central region of the body portion, including cutting the stretchable garment material along a curved path to yield, in each of the first and second articles, respective front and rear panel portions, wherein the front panel portions have a different surface area characteristic than the rear panel portions. For example, the rear panel can have a greater surface area and/or height or length characteristic relative to the front panel, or vice-versa.

Example 23 can include, or can optionally be combined with the subject matter of any of Examples 17 through 22 to optionally include, after separating the first article and the second article, forming a leg cuff along a perimeter of the first article that is opposite the waistband region of the first article.

Example 24 can include, or can optionally be combined with the subject matter of Example 23, to optionally include forming a continuous leg cuff along a perimeter of the first article that is opposite the waistband region of the first article, and along longitudinal edges of the first absorbent assembly.

Example 25 can include, or can optionally be combined with the subject matter of any of Examples 17 through 24 to optionally include, for the first article, joining front and rear panel portions of the first article using the first absorbent assembly, including attaching a first end region of the first absorbent assembly to the front panel portion and attaching an opposite second end region of the first absorbent assembly to the rear panel portion.

Example 26 can include, or can optionally be combined with the subject matter of any of Examples 17 through 25 to optionally include, for the first article, applying the first absorbent assembly to a portion of the outer facing surface of the first half of the body portion of the garment structure.

Example 27 can include, or can optionally be combined with the subject matter of Example 26, to optionally include, prior to packaging the first article, turning the first article inside-out such that the first absorbent assembly is positioned on a body-facing side of the article.

Example 28 can include, or can optionally be combined with the subject matter of one or any combination of Examples 1 through 27 to include, subject matter (such as an apparatus, a method, a means for performing acts, or a machine readable medium including instructions that, when performed by the machine, that can cause the machine to perform acts), such as can include a method for manufacturing a series of substantially seamless adult incontinence underwear products, the method including using a three-dimensional knitting machine to knit a substantially tubular first waistband region for a first article using a first material filament, using the same three-dimensional knitting machine to knit a substantially tubular garment structure for the first article using the same first material filament, the garment structure continuous with an end of the first waistband region and including a first open end, a continuous inner facing surface, and a continuous outer facing surface, using the same three-dimensional knitting machine to knit a substantially tubular garment structure for a second article using the same first material filament, the garment structure for the second article continuous with the garment structure for the first article, and cutting the substantially tubular garment structure to separate the garment structure for the first article from the garment structure for a second article. Example 28 can optionally include using the same three-dimensional knitting machine to knit a substantially tubular second waistband region for the second article using the first material filament, and knitting at least a portion of a substantially tubular third waistband region for a third article using the first material, the second and third waistband regions continuous with each other, and separating the second article from the third article at a junction between the second waistband region and the third waistband region.

Example 29 can include, or can optionally be combined with the subject matter of Example 28, to optionally include applying respective first and second absorbent assemblies to the first and second articles to provide respective first and second substantially seamless incontinence underwear products.

Example 30 can include, or can optionally be combined with the subject matter of Example 29, to optionally include, as the knitting the first waistband region for the first article, knitting the first material filament in a pattern that provides a first stretch characteristic, and wherein the knitting the tubular garment structure for the first article includes knitting the first material filament in a second pattern that provides a different second stretch characteristic.

Example 31 can include, or can optionally be combined with the subject matter of one or any combination of Examples 1 through 30 to include, subject matter (such as an apparatus, a method, a means for performing acts, or a machine readable medium including instructions that, when performed by the machine, that can cause the machine to perform acts), such as can include a disposable underwear garment for incontinent individuals, the garment including a substantially tubular knitted upper portion configured to be worn at or below a wearer's waist, the substantially tubular knitted upper portion including an extensible and retractable material that is substantially seamless about the circumference of the tubular upper portion, including being seamless in regions that are configured to be positioned at a wearer's hips, and an absorbent panel assembly having first and second end regions that are coupled to respective front and rear panel portions of the tubular knitted upper portion, and the absorbent panel assembly having an absorbent core that is positioned between a body-side layer and a liquid-impervious outside layer, and the absorbent core is configured to correspond to a body fluid insult area when the underwear garment is worn.

Example 32 can include, or can optionally be combined with the subject matter of Example 31, to optionally include a crotch panel having a body-side surface, the crotch panel extending between the front and rear panel regions of the tubular knitted upper portion to provide leg holes on opposite longitudinal sides of the crotch panel, and wherein the liquid-impervious outside layer of the absorbent panel assembly is coupled to the body-side surface of the crotch panel.

Example 33 can include, or can optionally be combined with the subject matter of Example 32, to optionally include the crotch panel is integrally formed and continuous with the substantially tubular knitted upper portion at one or both of the front and rear panel regions of the tubular knitted upper portion.

Example 34 can include, or can optionally be combined with the subject matter of any one of Examples 32 or 33 to optionally include the crotch panel is joined to one or both of the front and rear panel regions of the tubular knitted upper portion using one or more of heat, steam, adhesive, stitching, or flat stitching.

Example 35 can include, or can optionally be combined with the subject matter of any of Examples 31 through 34 to optionally include the tubular knitted upper portion includes a waistband region, a front panel region, and a rear panel region, and wherein a texture, density, or stretch characteristic of the waistband region differs from a texture, density, or stretch characteristic of at least one of the front and rear panel regions.

Example 36 can include, or can optionally be combined with the subject matter of any of Examples 31 through 35 to optionally include a waistband coupled to a first end of the substantially tubular knitted upper portion of the garment.

Each of the non-limiting examples described herein can stand on its own, or can be combined in various permutations or combinations with one or more of the other examples in this document, including in the figures and claims.

The above description is intended to be illustrative, and not restrictive. For example, the above-described examples (or one or more aspects thereof) may be used in combination with each other. Other embodiments can be used, such as by one of ordinary skill in the art upon reviewing the above description. In the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations.

The claimed invention is:

1. A method for manufacturing substantially seamless incontinence underwear products, the method including:
    manufacturing a substantially cylindrical garment structure using a stretchable garment material, the garment structure including first and second open end faces and a substantially cylindrical body portion between the first and second open end faces, the substantially cylindrical body portion of the garment structure including an inner facing surface, and an outer facing surface;
    at or near the perimeter edges of the first and second open end faces, preparing respective first and second waistband regions;
    separating the garment structure into first and second articles at a central region of the body portion, the first article including the first waistband area and substantially a first half of the body portion of the garment structure, and the second article including the second waistband area and substantially a second half of the body portion of the garment structure; and
    applying respective first and second separately provided absorbent assemblies to the first and second articles to provide respective first and second substantially seamless incontinence underwear products.

2. The method of claim 1, wherein the manufacturing the substantially cylindrical garment structure includes using a three-dimensional knitting machine to knit the garment structure using one or more garment material filaments.

3. The method of claim 1, wherein the manufacturing the substantially cylindrical garment structure includes molding, printing, or depositing the garment structure.

4. The method of claim 1; wherein the preparing the first waistband area includes preparing the first waistband area in a portion of the garment structure that extends from the perimeter edge of the first open end face toward a center of the garment structure, the first waistband area having a different texture, density, or stretch characteristic than the body portion of the garment structure.

5. The method of claim 1, wherein the preparing the first waistband area includes attaching a waistband material at the perimeter edge of the first open end face and extending from the first open end face away from a center of the garment structure, the waistband material having a different texture, density, or stretch characteristic than the body portion of the garment structure.

6. The method of claim 1, wherein the separating the garment structure into first and second articles at the central region of the body portion includes cutting the stretchable garment material along a curved path to yield, in each of the first and second articles, respective front and rear panel portions, wherein the front panel portions have a different surface area characteristic than the rear panel portions.

7. The method of claim 1, comprising, after separating the first article and the second article, forming a leg cuff along a perimeter of the first article that is opposite the waistband region of the first article.

8. The method of claim 7, wherein the forming the leg cuff includes forming a continuous leg cuff along a perimeter of the first article that is opposite the waistband region of the first article, and along longitudinal edges of the first absorbent assembly.

9. The method of claim 1, wherein the applying the absorbent assemblies includes, for the first article, joining front and rear panel portions of the first article using the first absorbent assembly, including attaching a first end region of the first absorbent assembly to the front panel portion and attaching an opposite second end region of the first absorbent assembly to the rear panel portion.

10. The method of claim 1, wherein the applying the absorbent assemblies includes, for the first article, applying the first absorbent assembly to a portion of the outer facing surface of the first half of the body portion of the garment structure.

11. The method of claim 10, including, prior to packaging the first article, turning the first article inside-out such that the first absorbent assembly is positioned on a body-facing side of the article.

12. A method for manufacturing a series of substantially seamless adult incontinence underwear products, the method including:
    using a three-dimensional knitting machine, knitting a substantially tubular first waistband region for a first article using a first material filament;

using the same three-dimensional knitting machine, knitting a substantially tubular garment structure for the first article using the same first material filament, the garment structure continuous with an end of the first waistband region and including a first open end, a continuous inner facing surface, and a continuous outer facing surface;

using the same three-dimensional knitting machine, knitting a substantially tubular garment structure for a second article using the same first material filament, the garment structure for the second article continuous with the garment structure for the first article;

cutting the substantially tubular garment structure to separate the garment structure for the first article from the garment structure for a second article;

applying a first absorbent assembly to the first article;

using the same three-dimensional knitting machine, knitting a substantially tubular second waistband region for the second article using the first material filament, and knitting at least a portion of a substantially tubular third waistband region for a third article using the first material, the second and third waistband regions continuous with each other;

separating the second article from the third article at a junction between the second waistband region and the third waistband region; and applying a different second absorbent assembly to the second article.

13. The method of claim 12, wherein the knitting the first waistband region for the first article includes knitting the first material filament in a pattern that provides a first stretch characteristic, and wherein the knitting the tubular garment structure for the first article includes knitting the first material filament in a second pattern that provides a different second stretch characteristic.

* * * * *